United States Patent [19]

Walter et al.

[11] Patent Number: 5,084,477
[45] Date of Patent: Jan. 28, 1992

[54] METHOD FOR THE TREATMENT OF NEMATODES IN SOIL USING FURFURAL

[75] Inventors: Gerald J. Walter, Lafayette, Ind.; Rodrigo Rodriguez-Kabana, Auburn, Ala.

[73] Assignee: Great Lakes Chemical Corporation, West Lafayette, Ind.

[21] Appl. No.: 615,217

[22] Filed: Nov. 19, 1990

[51] Int. Cl.$^5$ .............................. A01N 43/08
[52] U.S. Cl. ................................... 514/461
[58] Field of Search .......................... 514/461

[56] References Cited

U.S. PATENT DOCUMENTS 1,592,039  7/1926  Miner .................. 514/461

*Primary Examiner*—Allen J. Robinson
*Attorney, Agent, or Firm*—Woodard, Emhardt, Naughton Moriarty & McNett

[57] ABSTRACT

A method for the treatment of nematodes includes applying to the nematodes in the soil a nematicidal amount of furfural. The furfural is preferably impregnated into the nematode-infested soil. The furfural may be applied neat or suspended in a variety of liquid or solid carrier systems, and is applied to the soil by methods including mixing, fumigation and injection. The furfural has excellent nematicidal effect at low concentrations, is cost effective, and is not phytotoxic.

16 Claims, 1 Drawing Sheet

METHOD FOR THE TREATMENT OF NEMATODES IN SOIL USING FURFURAL

BACKGROUND OF THE INVENTION

1. Field of the Invention

This invention relates to the field of methods and chemicals for control of nematodes and other soil-borne pests, and particularly to a method using furfural as a nematicide.

2. Description of the Prior Art

Nematodes are slender, worm-like organisms found in the soil almost anywhere in the world. Nematodes reproduce bisexually and by parthenogenic or hermaphroditic reproduction which result in eggs, and then typically progress through four juvenile stages to adulthood.

A significant segment of the world's nematodes are plant parasitic, and more than one thousand species of nematodes are known to be harmful to plants. Most plant parasitic nematodes range from 0.5 to 3.0 mm in length. Many plants are affected by nematodes, including soybeans, peanuts, cotton, tobacco, strawberries, root crops, ornamentals, mint, alfalfa, squash, potatoes and many other crops. Nematodes feed on the roots and lower stems of plants, and some attack the leaves and flowers. Some species of nematodes inadvertently introduce pathogenic, root-invading microorganisms into the plants while feeding. Nematodes may also predispose plants to other disease causing agents, resulting in wilts and root rots. In other instances, the nematodes themselves cause the disease, disrupting the flow of water and nutrients in the xylem system, resulting in deprivation of the above-ground parts, and subsequently causing stunting and reduced fruitfulness. Symptoms of nematode infestation include swellings, thickenings, galls and distortions of above-ground components of the plant, and root conditions such as short stubby roots, lesions (dead spots), swellings, galls and deterioration of the plant. See, "The Mutagenicity of Pesticides" by Samuel S. Epstein and Marvin S. Legator, MIT Press, 1971.

The extent of crop loss to nematode infestation is substantial and widespread. The yield losses in agricultural crops in the United States and throughout the world are enormous, and have been labelled as "appalling" by experts in the field.

There is a substantial need for additional chemical controls to limit the damage caused by nematodes and to curb their spread to uninfested fields, especially now because some effective materials have been withdrawn from the marketplace. Nematicides have been available in the prior art, some of which were useful as fumigants. The most effective and widely used control agents have been methyl bromide and EDB (ethylene dibromide), and certain chlorinated compounds including D-D (1,3-dichloropropene-1,2-dichloropropane), DBCP (1,2-dibromo-3-chloropropane), and Telone (1,3-dichloropropene). Other nematicides generally fall within three groups: (1) organophosphate insecticides, (2) isothiocyanates, and (3) carbamate or oxime insecticides. In U.S. Pat. No. 5,013,762 (Ser. No. 442,314, filed Nov. 28, 1989), issued to Smith et al. on May 7, 1991, the use of bromonitromethane as a nematicide has recently been described.

Some of the better known nematicides have been in use for many years. The nematicidal properties of DD and EDB, for example, were discovered in 1943 and 1945 respectively, and effectively launched the use of fumigant nematicides on a field-scale basis. Prior to the 1940's only seedbeds, greenhousebeds, and potting soil had been treated using materials such as chloropicrin (trichloronitromethane), carbon disulfide and formaldehyde. These were very expensive, in some instances explosive, and usually required a surface seal because of their relatively high vapor pressures. See, "The Pesticide Book" by George W. Ware, W. H. Freeman & Co., 1978.

Many of the time-tested nematicides, however, have fallen by the wayside because of carcinogenicity, toxicity and environmental problems. DBCP, for example, was found to be relatively inexpensive and effective, but has been removed from the market because of a tendency to reduce sperm counts in males, and also because of mutagenic activity. Methyl bromide, a highly effective product, is lethal to plant and animal life, and therefore should be used at least two weeks before planting to avoid its total phytotoxic effect. Attempts to substitute non-fumigants have been mostly unsuccessful because of the expense or the limited efficacy of those materials.

Reference to other chemical pesticides has not proven to be very helpful. There are numerous forms of pesticides adapted to the treatment of particular pests. These include, for example, insecticides, herbicides, fungicides, rodenticides, bactericides, acaricides, algicides, miticides, molluscicides, avicides, slimicides, piscicides and ovicides, as well as disinfectants, growth regulators, defoliants, desiccants, repellents, attractants and chemosterilants. The operation of the different types of pesticides varies according to the pests being treated. For example, the known or suspected major modes of chemicals for treating plants (including herbicides, fungicides, etc.) include: (a) inhibition of photosynthesis, (b) inhibition of oxidative phosphorylation, (c) hormone analogs, (d) inhibition of pantothenate synthesis and (e) inhibition of porphyrin, hence of chlorophyll synthesis. In contrast, the operation of chemicals for the treatment of animals (insecticides, nematicides, etc.) include: (a) inhibition of acetylcholinesterase, (b) inhibitions of neuromuscular junction and (c) neurotoxication. There have consequently been a vast number of known pesticides covering a large variety of chemicals operating in differing fashions. However, few effective nematicides have been discovered in the prior art.

There has therefore remained a longstanding and substantial need for a nematicide which is effective, and does not have the disadvantages of the prior art chemicals. The elimination of cheap, effective fumigant nematicides and the poor performance of remaining controls are forcing some crops out of production in the traditional nematode-infested areas of the United States. Also, some nematodes are beginning to appear in areas never before troubled by these pests, as evidenced by the appearance of the soybean cyst nematode in the midwestern United States. While the need continues to grow, concerns over the inherent human toxicity of contact nematicides, and environmental problems from high rates of application (such as leaching into ground water) will result in the restriction of some of the remaining known products.

The present invention is based upon the discovery that furfural is effective as a nematicide, and does not have the high expense or human toxicity associated with certain prior art compounds. Furthermore, furfural is a natural product readily extracted from a wide variety of vegetation, and is known to occur naturally in products routinely consumed by humans. Heretofore, furfural has been indicated as useful for a variety of purposes, including as a fungicide or weed killer. See, The Condensed Chemical Dictionary, Van Nostrand Reinhold Co. (10th Ed. 1981). Also, there are reports in the literature of aromatic aldehydes having antimicrobial and antifungal properties. Benzaldehyde and cinnamaldehyde have been reported as insecticides for use on stored grain. However, it is believed that none of the latter described aldehydes have ever been used commercially. See, Proceedings of the Association for Plant Protection of Kyushu 1987 by Ishibashi, N and Kubo, H. at Saga University. Japan.

SUMMARY OF THE INVENTION

Briefly describing one aspect of the present invention, there is provided a method for treating nematodes which includes applying to the nematodes in the soil a nematicidal amount of furfural. The furfural is applied by a variety of methods, such as impregnation into the infested soil by fumigation or injection. The furfural may be suspended in a suitable carrier system. Other chemicals including herbicides, fungicides or the like may be mixed, where compatible, with the furfural and applied to the soil simultaneously.

It is an object of the present invention to provide a highly effective and cost-efficient method for the control of nematodes.

Another object of the present invention is to provide a method for treating nematodes in nematode-infested soil, which method is readily accomplished by fumigation and is effective against adult nematodes, their larvae, and the eggs.

A further object of the present invention is to provide a method for controlling nematodes which utilizes a natural product, thereby minimizing the potential for environmental concerns.

It is another object of the present invention to provide a method for controlling nematodes which avoids the disadvantages of prior art chemicals and methods such as mammalian toxicity, environmental contamination and the potential for residues on food stuffs.

Further objects and advantages of the present invention will be apparent from the description of the preferred embodiment which follows.

DESCRIPTION OF THE PREFERRED EMBODIMENT

Figure 1:
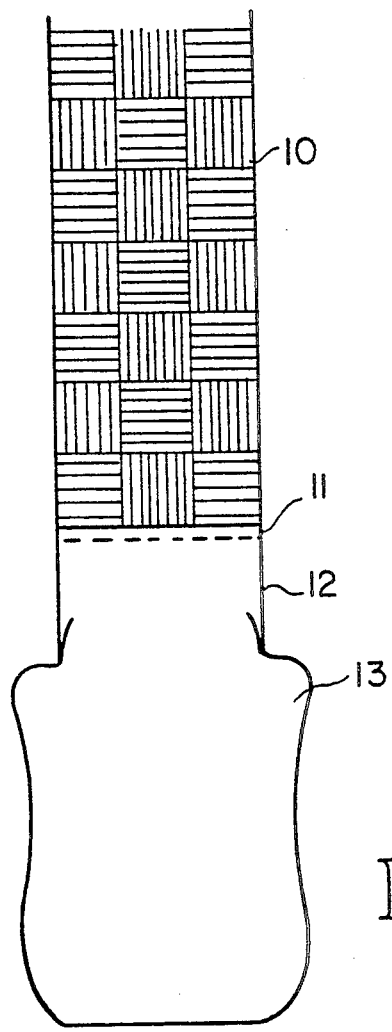
FIG. 1 is a schematic view of a test apparatus used to demonstrate the efficacy of furfural as a nematicide when applied to infested soil.

For the purposes of promoting an understanding of the principles of the invention, reference will now be made to the preferred embodiments thereof and specific language will be used to describe the same. It will nevertheless be understood that no limitation of the scope of the invention is thereby intended. Alterations and further applications of the principles of the invention are contemplated as would normally occur to one skilled in the art to which the invention relates.

There has remained a substantial and long felt need for a new nematicide which has the combined advantages of good efficacy, low cost, low toxicity to humans, and low environmental impact. Various nematicides have been provided in the prior art, but these have generally been deficient in one or more of these areas. In fact, several prior art nematicides have been banned or severely restricted as to use, and others are unacceptably low in efficacy or high in cost. With the considerable losses in crop yield which are attributable to plant-parasitic nematode infestation, the need for a useful nematicide has continued.

The present invention involves the application of a nematicidal amount of furfural to nematodes in infested soil. The chemical itself has been known almost 100 years. However, the present invention is based on the unexpected discovery that furfural is a highly effective nematicide. It is useful in controlling all stages of nematodes, and is particularly effective.

Furfural has been found to be useful in controlling nematodes and other soil born pests, even when applied in limited quantities to infested soil. As used herein, the term "soil" is intended to encompass any plant growth medium. The rate of use may vary somewhat with the nature of the soil, including density, porosity, constituents, etc. Also, the rate may vary according to the species of nematodes, the degree of infestation, and the manner of application of the furfural. It has been determined, however, that furfural is volatile and will therefore permeate the soil rapidly and widely. As demonstrated in the specific examples herein, furfural is effective against adult nematodes, their larval forms, and encysted nematodes.

The preferred method of applying furfural to the soil is by spraying the neat liquid or applying it with a carrier. Suitable carriers include organic diluents such as petroleum distillates. Alternatively, aqueous compositions may be prepared by dispersing the furfural in water with an appropriate dispersing or emulsifying agent. Furfural may be absorbed onto a porous substrate such as corn cob grit or other finely divided solids such as chalk, talc, fullers earth or a clay, which would serve as a carrier. Another type of carrier is the reaction product of furfural with alcohols, amines, and related chemicals to form a totally new chemical species which would release furfural under conditions prevalent in moist soils.

Furfural is applied to the soil in a nematicidal amount. The level of application, depending on several factors, is preferably established in terms of the amount which provides the desired nematicidal effect under the use conditions. For example, the preferred usage is at the minimum nematicidal rate. Good results are obtained when the furfural is present in the soil in an amount between 4 and 240 parts of furfural per million parts of the soil. A preferred rate of application is between 8 and 160 parts of furfural per million parts of the soil. It is a feature of the present invention that the furfural is efficacious when used at low levels, namely less than about sixteen ppm of soil.

The furfural is advantageously applied to soil at a rate to achieve the foregoing concentrations, for example at a rate of between 0.01 and 2.0 ml of furfural per kilogram of soil. In a preferred embodiment, the soil is treated with between 0.1 and 1.0 ml of furfural per kilogram of soil. A most preferred rate of application is about 0.5 ml of furfural per kg of soil. One aspect of the present invention is that the furfural is effective at rates below about 0.25 ml per kg of soil.

In field applications, furfural is applied to the soil to treat the surface layer in which the nematodes reside.

Typically, the treatment is directed at the top several inches of soil, perhaps as little as a few inches or as much as ten to twelve inches. The furfural is preferably injected at a depth of 7-10 inches or deeper, having the shanks spaced 8 to 10 inches apart. The amount of furfural applied to the soil is selected to achieve furfural concentrations as previously indicated, and is efficaciously in the range of 1 to 40 gallons per acre of soil. A more preferred application rate is between 8 and 20 gallons furfural per acre of soil, with the most preferred rate being about 15 gallons per acre.

It will be appreciated that the selected method and rate of application will depend somewhat on the conditions of the soil, the crop and the infestation. The underlying consideration is the application of a nematicidal amount of furfural, i.e., an amount of furfural which will give the desired nematicidal effect under conditions of use. The desired amount may be affected by the method of application, the temperature or other conditions of the soil or air, the form of the composition (liquid, solid or vapor), and the ingredients of the composition. The selected rate may also be affected by the nature of the infestation, including the species of nematodes, the condition of the nematodes (encysted, etc.), and the extent of infestation. Generally, the furfural has been found not to be phytoxic and not to leave soil residues harmful to plants.

Furfural may be applied to the soil prior to or at planting. For transplanted crops (e.g. tobacco), fumigants are usually applied two weeks or more before planting. For seeded crops (soybean, peanut, cotton, etc.), application at or near planting time is usually acceptable. In some applications, fumigant, seed and fertilizer are applied concurrently or simultaneously.

Furfural may be prepared in concentrated form for later application upon dilution. Suitable formulations, particularly those employing an aqueous system, may be prepared in this manner.

The unexpected and significant efficacy of furfural as a nematicide is illustrated by the following examples.

EXAMPLE 1

Soil was collected from a field located on the Auburn University Wiregrass Substation at Headland, Alabama. This field was selected as being naturally infested with various types of nematodes, namely *Meloidogyne arenaria* and *M. incognita* (root-knot), *Heterodera glycines* (soybean-cyst), *Pratylenchus brachyurus* (lesion), *Helicotylenchus dihystera* (spiral) and also the non-parasitic nematodes *Aphelenchus* spp., Dorylaimida and saprophytic or or microbivorous (mostly Rhabditida) types.

To treat the soil collected from Headland, Alabama, it was placed in a plastic bag. Then furfural at a level of 0.1 ml/kg soil was injected into this bag and the bag was shaken to help distribution. The soil was then transferred to a pot and removed to a greenhouse. The above exercise was repeated seven times to provide eight replicates of each treatment level. Additional treatment levels were 0.2, 0.5, 0.75 and 1.0 ml of furfural per kg of soil plus a control or untreated soil sample for comparison purposes. Eight replicas of each treatment level including the control were prepared. One week after treatment, 100 grams of soil were removed from each container and assayed for populations of nematodes. Standard incubation techniques were used for enumeration of nematode populations. The results are reported in Table 1.

TABLE 1

| Treatment | Rate (ml/kg soil) | Root-Knot Larvae | Lesion | Dorylaimoid | Saprophagous |
|---|---|---|---|---|---|
| 1 Control |  | 94.9 | 4.5 | 6.4 | 222.4 |
| 2 Furfural | 0.10 | 66.5 | 2.6 | 1.6 | 169.6 |
| 3 Furfural | 0.20 | 16.8 | 0.3 | 2.5 | 160.0 |
| 4 Furfural | 0.50 | 0.0 | 0.0 | 0.0 | 48.8 |
| 5 Furfural | 0.75 | 0.0 | 0.0 | 0.0 | 0.4 |
| 6 Furfural | 1.00 | 0.0 | 0.0 | 0.0 | 0.0 |

As shown above in Table 1, furfural at concentrations at least as low as 0.1 ml/kg were effective in reducing nematode populations, and at levels of 0.5 ml/kg of soil and above the furfural was highly effective in controlling the larva of Root-Knot nematode and nematodes from the species of Lesion, Dorylaimoid and Saprophagous. Application rates as low as about 0.01 ml furfural per kg of soil, and as high as 2.0 ml/kg, also yield reduced nematode population.

EXAMPLE 2

The procedure of Example 1 was repeated except that seven days after soil treatment with furfural crookneck squash was planted in the treated and control soils. The results after 60 days show excellent control of the Root-Knot nematodes larva as well as other plant-parasitic nematodes (lesion, stubby root), while allowing survival of the Dorylaimoid and Saprophagous nematodes. (Table 2a)

TABLE 2a

| Treatment | Rate (ml/kg soil) | Root-Knot Larvae | Lesion | Stubby Root | Dorylaimoid | Saprophagous |
|---|---|---|---|---|---|---|
| 1 Control |  | 32.3 | 9.7 | 12.8 | 20.8 | 173.7 |
| 2 Furfural | 0.10 | 12.0 | 4.1 | 6.0 | 11.9 | 231.8 |
| 3 Furfural | 0.20 | 5.8 | 0.4 | 0.0 | 5.9 | 206.9 |
| 4 Furfural | 0.50 | 0.0 | 0.0 | 0.0 | 7.0 | 511.8 |
| 5 Furfural | 0.75 | 0.0 | 0.0 | 0.0 | 1.8 | 736.5 |
| 6 Furfural | 1.00 | 0.0 | 0.0 | 0.0 | 2.1 | 703.1 |

A second method of observing nematode population effects due to a nematacidal treatment is to observe the root condition and plant development of host crop grown in treated infested soil. Furfural was extremely effective in allowing shoot development in crookneck squash. Also, the gall rates on the roots of treated plants were less than on the control. The Pertinent observations are set forth in Table 2b.

TABLE 2b

| Treatment | Rate (ml/kg soil) | Top Height (cm) | Top Weight (g) | Root Weight (g) | Root Condition | Galls/g Fresh Root | Gall Rate |
|---|---|---|---|---|---|---|---|
| 1 Control |  | 18.5 | 4.65 | 1.27 | 3.6 | 57.6 | 6.1 |
| 2 Furfural | 0.10 | 19.4 | 5.14 | 1.11 | 3.6 | 51.0 | 6.0 |
| 3 Furfural | 0.20 | 20.6 | 4.39 | 0.98 | 3.7 | 22.0 | 5.1 |
| 4 Furfural | 0.50 | 19.9 | 5.21 | 0.85 | 3.8 | 00.1 | 0.0 |
| 5 Furfural | 0.75 | 20.1 | 5.23 | 1.26 | 4.0 | 00.8 | 0.5 |
| 6 Furfural | 1.00 | 19.8 | 5.29 | 1.02 | 3.7 | 00.0 | 0.0 |

EXAMPLE 3

A predetermined amount of furfural was injected into a plastic bag containing Headland soil. The bag was shaken well to insure even distribution, and the soil was then transferred to a container for stabilization followed by a determination of nematode levels. Soil applications by fumigation with furfural were also prepared and the soil infestation evaluated.

Fumigation properties of furfural were determined using the apparatus depicted in FIG. 1. Soil was placed in a 7.6 cm diameter PVC cylinder 10 that was 17.5 cm long. A 1 mm mesh fiberglass screen 11 overlaid with a disc of Whatman No. 1 filter paper (not shown) prevented the soil from falling through the cylinder. The cylinder was glued to a second 4.5 cm long cylinder 12. The whole structure was glued with silicone rubber to a square wide mouth 15.5 cm diameter 900 ml capacity glass jar 13. Furfural was injected through an injection port in the jar collar to volatilize through the soil column. The injection port was then resealed with silicone rubber. The results, reported in Tables 3a and 3b, show good control of nematode type pests when furfural is injected into the soil or applied as a fumigant.

TABLE 3a

| | In-Soil Application Nematodes/100 cc Soil | | | |
|---|---|---|---|---|
| Treatment | Rate (ml/.5 kg soil) | Root-Knot Larvae | Lesion | Doryl-aimoid | Sapro-phagous |
| 1 Control | | 140.7 | 2.6 | 12.0 | 181.4 |
| 2 Furfural | 0.20 | 7.3 | 0.0 | 0.0 | 49.1 |
| 3 Furfural | 0.50 | 0.9 | 0.0 | 0.0 | 0.4 |
| 4 Furfural | 1.00 | 0.0 | 0.0 | 0.0 | 0.0 |
| 5 Furfural | 1.50 | 0.0 | 0.0 | 0.0 | 0.0 |
| 6 Furfural | 2.00 | 0.0 | 0.0 | 0.0 | 0.0 |

TABLE 3b

| | Fumigant Application Nematodes/100 cc Soil | | | |
|---|---|---|---|---|
| Treatment | Rate (ml/.5 kg soil) | Root-Knot Larvae | Lesion | Doryl-aimoid | Sapro-phagous |
| 1 Control | | 153.4 | 1.3 | 14.2 | 188.3 |
| 2 Furfural | 0.10 | 48.6 | 0.0 | 3.5 | 132.6 |
| 3 Furfural | 0.25 | 9.9 | 0.4 | 6.1 | 40.9 |
| 4 Furfural | 0.50 | 0.0 | 0.0 | 1.6 | 7.3 |
| 5 Furfural | 0.75 | 0.3 | 0.0 | 0.0 | 10.9 |
| 6 Furfural | 1.00 | 0.0 | 0.0 | 0.0 | 2.6 |

EXAMPLE 4

Repetition of the foregoing Examples using various carrier systems, as described previously, and for various other plants, yields similar results. Also, the foregoing Examples 1-3 simulate applications of furfural to soil at rates described previously in terms of parts per million or gallons per acre. The application of the furfural by various means, such as injection or fumigation of the soil, to achieve the same indicated levels of furfural in the soil produces similar good results.

EXAMPLE 5

The furfural is combined with other chemical treatments including insecticides, fungicides, herbicides, etc. and applied to the soil or directly to nematodes. Application in accordance with the various foregoing carrier systems and treatment methods results in effective nematicidal treatment of the soil.

In view of the above, it will be seen that the several objects of the invention are achieved and other advantageous results attained. As various changes could be made in the above process, compositions and systems without departing from the scope of the invention, it is intended that all matter contained in the above description shall be interpreted as illustrative and not in a limiting sense.

What is claimed is:

1. A method for the treatment of nematodes in soil which comprises applying to the nematodes in the soil a nematicidal amount of furfural.

2. The method of claim 1 in which said applying comprises impregnating the soil by an application process selected from the group consisting of: mixing, fumigation and injection.

3. The method of claim 2 in which said impregnating comprises fumigating the soil with a nematicidal amount of furfural.

4. The method of claim 1 in which said applying comprises impregnating the soil with furfural in the amount of between 4 and 240 parts of furfural per million parts of the soil.

5. The method of claim 4 and which comprises impregnating the soil with furfural in the amount of between 8 and 160 parts of furfural per million parts of the soil.

6. The method of claim 4 and which comprises impregnating the soil with furfural in the amount of less than about 16 parts of furfural per million parts of the soil.

7. The method of claim 1 and which comprises applying the furfural to the soil in the amount of between 1 and 40 gallons of furfural per acre of the soil.

8. The method of claim 7 and which comprises applying the furfural in the amount of between 8 and 20 gallons of furfural per acre of the soil.

9. The method of claim 8 and which comprises applying the furfural in the amount of about 15 gallons of furfural per acre of the soil.

10. The method of claim 1 and which comprises applying the furfural to the soil in the amount of between 0.01 and 2.0 ml of furfural per kg of the soil.

11. The method of claim 10 and which comprises applying the furfural in the amount of between 0.1 and 1.0 ml of furfural per kg of the soil.

12. The method of claim 11 and which comprises applying the furfural in the amount of between 0.5 and 1.0 ml of furfural per kg of soil.

13. The method of claim 1 in which said applying comprises applying to the nematodes in the soil a composition including furfural and a carrier system.

14. The method of claim 13 and which comprises applying an aqueous emulsion of the furfural.

15. The method of claim 13 and which comprises applying a composition consisting essentially of furfural and an inert carrier.

16. The method of claim 15 and which comprises applying an aqueous emulsion of the furfural.

* * * * *